United States Patent [19]

Udagawa et al.

[11] Patent Number: 5,041,689
[45] Date of Patent: Aug. 20, 1991

[54] METHOD OF RECOVERING L-QUEBRACHITOL FROM RUBBER LATEX SERUMS

[75] Inventors: Yoshitaka Udagawa, Tokyo; Morihisa Machida, Kanagawa; Seiichiro Ogawa, Musashino, all of Japan

[73] Assignees: The Yokohama Rubber Co., Ltd., Tokyo, Japan; The Board of the Rubber Research Institute of Malaysia, Kuala Lumpur, Malaysia

[21] Appl. No.: 372,479

[22] Filed: Jun. 28, 1989

[30] Foreign Application Priority Data

Jul. 6, 1988 [JP] Japan .............................. 63-168563

[51] Int. Cl.⁵ ..................... C07C 41/34; C07C 41/40

[52] U.S. Cl. .................................... 568/670; 568/699
[58] Field of Search .............................. 568/670, 699

[56]      References Cited

U.S. PATENT DOCUMENTS

1,758,616  5/1930  McGavack et al. .

Primary Examiner—Werren B. Lone
Assistant Examiner—Margaret Argo
Attorney, Agent, or Firm—Finnegan, Henderson, Farabow, Garrett & Dunner

[57] ABSTRACT

Purified L-quebrachitol is recovered in increased quantities from rubber latex by dissolving concentrated solutions or pulverized solids of the serums in methyl alcohol under specified extraction conditions.

7 Claims, 11 Drawing Sheets

METHOD OF RECOVERING L-QUEBRACHITOL FROM RUBBER LATEX SERUMS

BACKGROUND OF THE INVENTION

1. Technical Field

This invention relates to a method of recovering or otherwise isolating L-quebrachitol from rubber latex serums.

2. Prior Art

L-Quebrachitol, chemically known to be a monomethyl ether of L-inositol, is widely found in quebraco barks, para rubber trees called Hevea brasiliensis and various other plants. This compound is termed L-(−)-2-O-methyl-chiroinositol.

Inositols are cyclohexanehexols having six hydroxyl groups bonded on the cyclohexane nucleus, They are stereoisomeric in structure and have nine isomers, among which the myoinositol is most abundant in the natural world. It exists as a phosphoric ester in plants and as a phosphatidyl inositol in organisms and animals. Such an isomer is important from the biochemical point of view, and certain of its derivatives have been used as essential components for some antibiotics. To this end, many studies have been made of the synthesis of various inositol derivatives particularly in the form of their phosphoric esters for biological use.

L-Quebrachitol, because of its optical activity, may act as a physiologically active material for organisms and also as a starting material for pharmaceutical products and agricultural chemicals. This compound, however, is currently available from rubber latex serums on a rather small scale.

It has been proposed that L-quebrachitol be recovered from rubber latex serums as disclosed in U.S. Pat. No. 1,758,616. This prior method is directed to extracting L-quebrachitol from serum solids with the use of a hot alcohol such as ethanol, propanol, butanol or the like, followed by concentration, cooling and deposition of the extract. Such heating mode of recovery is hazardous and costly and liable to entrain eluates other than L-quebrachitol which adversely affects the purity of the final compound.

Rubber latex serums have in most instances been discarded as waste solutions in countries in which rubber trees are cultivated to produce natural rubber. It is known that those serums can be evaporated into a particulate material for use as a rubber processing additive as taught by Japanese Patent Laid-Open Publication No. 63-161002.

SUMMARY OF THE INVENTION

With the foregoing difficulties of the prior art in view, the present invention seeks to provide a new and improved method enabling L-quebrachitol to be recovered, with utmost efficiency, at high purity and in large quantity, from rubber latex serums heretofore discarded.

L-Quebrachitol according to the invention finds utility as a starting material or an intermediate product for medicinal preparation and also as a food additive and further in other industrial sectors.

More specifically, as will become better understood from the following description, the invention provides a method of recovering an L-quebrachitol compound from a rubber latex serum, which comprises treating the serum into an extractible condition, dissolving the serum in methanol to thereby extract L-quebrachitol, depositing the extract, and subsequently separating and collecting the deposit from the solution.

BRIEF DESCRIPTION OF THE DRAWINGS

FIG. 2A through FIG. 5A are views similar to FIG. 1A, but illustrative of the spectra of the compound as measured respectively by IR spectrometry, differential scanning calorimetry, gas chromatography and $^1$H-NMR spectrometry.

FIG. 1B through FIG. 5B are views showing the spectra of an L-quebrachitol species reported by a certain academic organization, such spectra being taken to identify the data of FIG. 1A to FIG. 5A.

DETAILED DESCRIPTION OF THE INVENTION

According to a method contemplated under the present invention, L-quebrachitol is recovered and isolated from serums by extraction with selected alcohols and under specified conditions.

By the term serum used herein is meant an aqueous solution byproduced upon coagulation of and subsequent removal of all rubber components from a natural rubber latex. The serum is usually composed of small amounts of proteins, nitrogeneous compounds, saccharides and the like. Contained in the saccharides is L-quebrachitol to be recovered by the invention. To attain simplified treatment and increased efficiency, the serum may preferably be used in the form a concentrated solution or a pulverized solid hereinafter referred to as a serum product.

In the practice of the invention, a selected serum product is dissolved in an alcohol to thereby extract L-quebrachitol. Importantly, the dissolution and extraction steps should be effected in methanol. Ethanol extraction, in place of methanol extraction, is not wholly satisfactory as the serum product is prone to become too viscous on the surface and hence practically impossible of filtration or separation.

According to the invention, the most desirable extraction temperature is in the range of from −20° to +40° C. Temperatures lower than −20° C. would entail extra, costly cooling equipment. Extraction at temperatures higher than 40° C. would require heating of methanol which would oftentimes render the resulting L-quebrachitol compound physically vulnerable in respect of melting point, color shade and other important qualities and yet involve adverse working atmosphere with high vapor pressure of the alcohol.

Methyl alcohols suitable for the purpose of the invention are preferably anhydrous in grade, but may be feasible even in a hydrous grade having a water content up to 30%. The alcohol may be added in an amount sufficient to fully dissolve a given serum product, generally from 200 to 1,000 ml per 100 g of the serum product.

Upon completion of the extraction, the solution is concentrated in vacuo, after which the concentrate is disposed usually overnight at room temperature so as to facilitate crystal growth. L-Quebrachitol thus deposited is filtered and collected usually in a yield of about 15 g based on 100 g of the starting serum product.

To further increase the purity of the L-quebrachitol product, the above deposit may preferably be recrystallized to remove small amounts of inorganic ions and other foreign matters coming from the serum. One such treatment may be accomplished for instance by dissolving the deposit in distilled water, followed by decoloration for example with active carbon and by removal of the decolorant on filtration and subsequently by passing the resulting solution through any suitable ion exchange resin. Ethanol is thereafter added until the solution is rendered turbidly white, this white component being L-quebrachitol. The alcoholic solution is let to stand at low temperature as in a refrigerator to thereby promote crystal growth and deposition. The recrystallizate is filtered and collected. The yield on purification has now been found to lie in the vicinity of 10 g per 100 g of the serum product.

The L-quebrachitol compound provided by the invention has been examined on the analyzers given below and with the results shown in FIG. 1A to FIG. 5A.

1. X-Ray Diffraction, Rotarflex, Rigaku Denki Co.
2. IR Spectrometry, 983G Type, Perkin-Elmer Co.
3. Differential Scanning Calorimetry, 910 Type, E. I. DuPont Co.
4. Gas Chromatorgaphy, 164 Type, Hitachi, Ltd.
5. $^1$H-NMR Spectrometry, JNMGX-400FT, JEOL, Ltd., under conditions of solvent: heavy water ($D_2O$) and internal standard: 3-trimethylsilyl-1-propane sodium sulfonate (DSS)

$^1$H-NMR analysis shows that the L-quebrachitol compound has a highly pure singlet peak corresponding to three peaks of a methine proton having bonded five hydroxyl groups, of another metine proton containing a methoxy group and of a methoxy group alone. Differential scanning calorimetry confirms that the compound melts at 184.5° C. which approximates closely to the melting point of 190° to 194° C. appearing in the article of L. Anderson, "The Carbohydrates", vol. 1 A, p. 519 (1972), Academic Press, New York.

The spectra of FIG. 1A to FIG. 5A have been found fully agreeable with those reported by Professor Ogawa's Research Laboratory, Keio University, and illustrated for purposes of identification in FIG. 1B to FIG. 5B, the report having been published in "Synthesis of Aldohexoses from L-Quebrachitol" by N. Senda, M. Suzuki and S. Ogawa, 56th Spring Symposium Preprints No. II, B18, the Chemical Society of Japan (1988). The compound according to the invention is thus confirmed to be L-quebrachitol.

The method of the invention is characterized by the recovery of L-quebrachitol with great ease and at high purity as compared to the prior art method in which acetylation is required to separate such compound.

The present invention will now be described by way of the following examples which are provided for illustrative purposes and should not be construed as limiting the invention.

EXAMPLE 1

A rubber latex serum previously concentrated was spray-dried to give a solid material. The dry solid was dissolved with stirring at a temperature range between 12 and 20° C. and in methanol of first-class reagent grade to thereby extract L-quebrachitol. The solvent was used in an amount of 750 ml per 100 g of the solid. Insoluble matter in the solution was filtered with mild suction on filter paper, Advantec No. 2, after which a reddish brown filtrate was obtained. The insolubles were washed with a small amount of methanol, thereby providing a white material left on the filter paper, which material was identified by X-ray diffraction to be inorganic in nature and predominantly ammonium sulfate.

The filtrate was concentrated to a one-tenth volume by vacuum distillation at 40° C. and then left overnight at room temperature (10° to 22° C). The resulting crystallizate was filtered and collected to provide crude L-quebrachitol in a yield of about 15 g per 100 g of the serum solid.

Thereafter, purification was done by dissolving the crude product in distilled water and by decoloring the solution with a limited amount of active carbon, followed by filtration and by subsequent passage through an ion exchange resin. Ethanol was added until the filtrate was rendered turbidly white, the turbidity being caused by the presence of L-quebrachitol. The alcoholic solution was allowed to stand overnight in a refrigerator and filtered to obtain about 10 g of pure L-quebrachitol.

The pure product was analyzed by X-ray diffraction, IR spectrometry, differential scanning calorimetry, gas chromatography and $^1$H-NMR spectrometry with the results shown in FIGS. 1A, 2A, 3A, 4A and 5A. It was identified to be L-quebrachitol in nature.

EXAMPLE 2

The effects of solvents were examined between methanol and ethanol.

(1) Room Temperature Test 50 g of a dry solid derived from a serum was added respectively with 500 ml of methanol and 500 ml of ethanol and stirred at a temperature range from 12° to 22° C. for 20 hours, followed by concentration to a 1/10 volume by vacuum distillation at from 40° to 45° C. The resulting crystallizate was dissolved in double the amount of distilled water and turbidified white by addition of ethanol. The solution was disposed at about 7° C. in a refrigerator to thereby obtain a recrystallizate which was then filtered and dried.

(2) Boiling Test

Two test solutions were prepared by dissolving 50 g of a similar solid in 500 ml of methanol and 500 ml of ethanol. The solutions were refluxed for one hour and filtered while being still hot, followed by successive treatment as was done in test (1).

The results of both tests are tabulated below. The inventive methanol recovery at room temperature has been found highly satisfactory in respect of the yield, color, melting and extractability characteristics as compared to the hot ethanol recovery of the foregoing prior art.

EXAMPLE 3

The effects of methanol at varied temperatures were examined on the yield and melt peak temperature of L-quebrachitol.

100 g of a serum dry solid was taken into methanol previously adjusted in its temperature at -17, 6, 20, 30 and 40° C. Each mixture after being stirred was disposed at the corresponding temperature for 48 hours. Insolubles were removed by filtration, and the filtrate was concentrated to a 1/10 volume by vacuum evaporation at 40° C. The concentrate was let to stand overnight at room temperature (9° to 23° C.), giving a deposit which was then filtered and collected.

The resulting crystallizate was dissolved in a doubled amount of distilled water, followed by addition of ethanol until the solution was turbidified white and by subsequent disposition at about 7° C. in a refrigerator for 48 hours. The recrystallizate was filtered and dried to provide an L-quebrachitol compound at the yield given in FIG. 6 and with the melting point shown in FIG. 7.

Figure 1A:
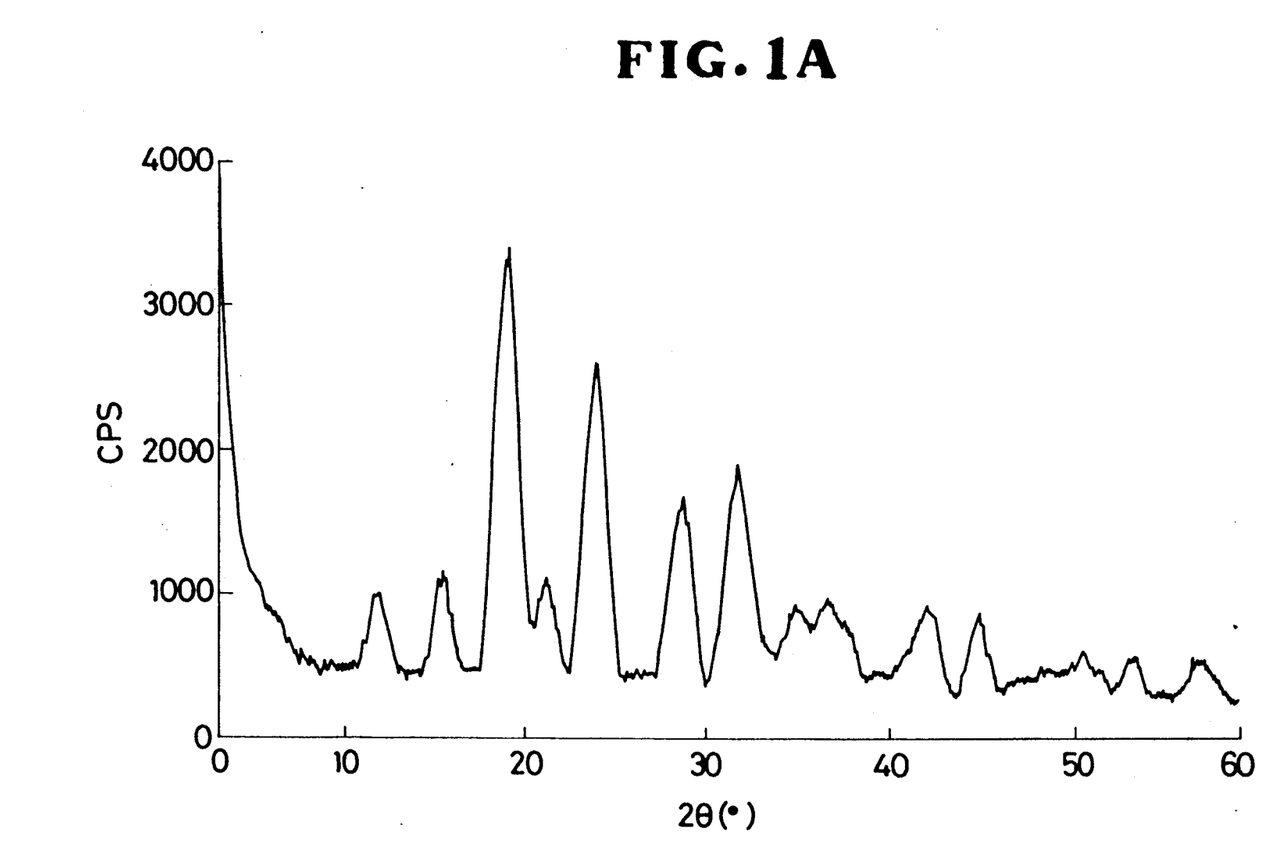
FIG. 1A is a spectral representation of an L-quebrachitol compound provided in accordance with the present invention and determined by X-ray diffraction.
Figure 1B:
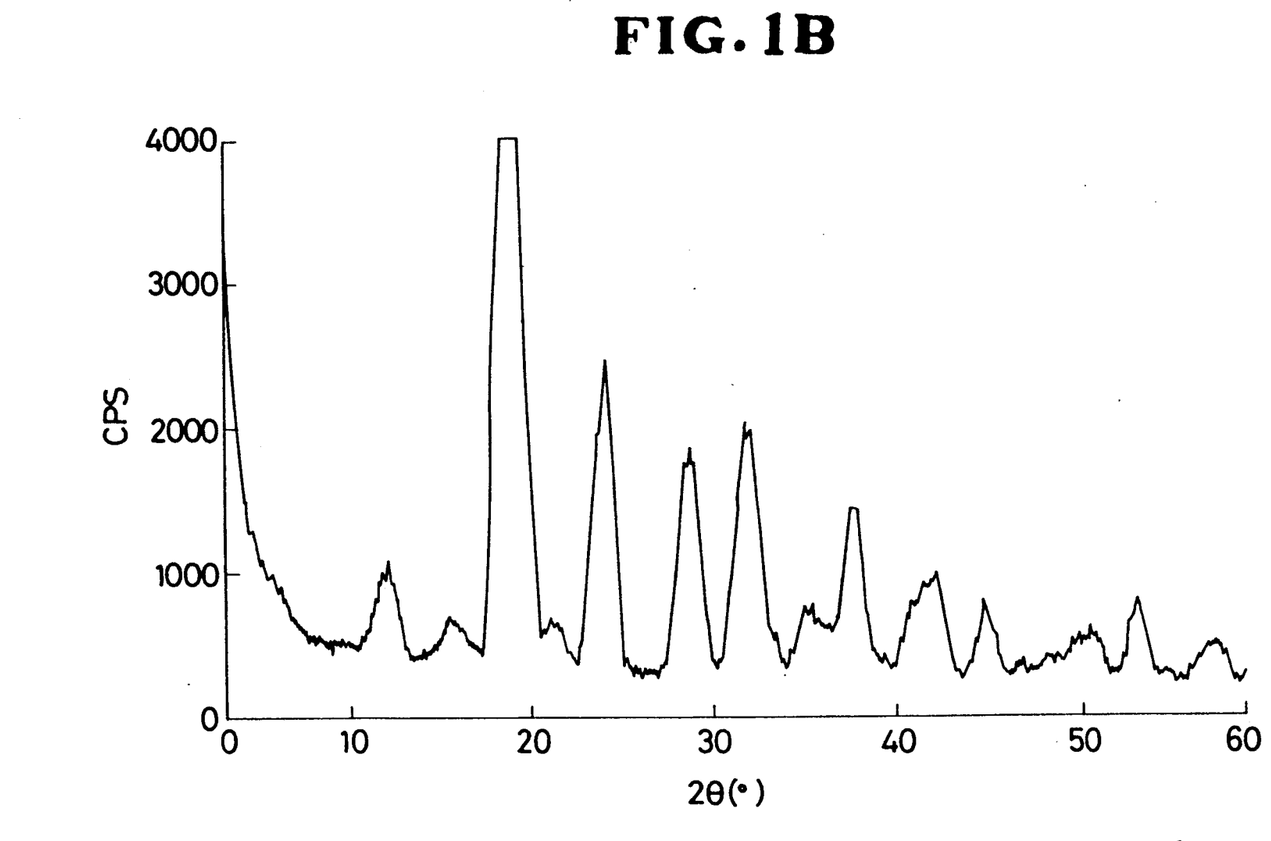
Figure 2A:
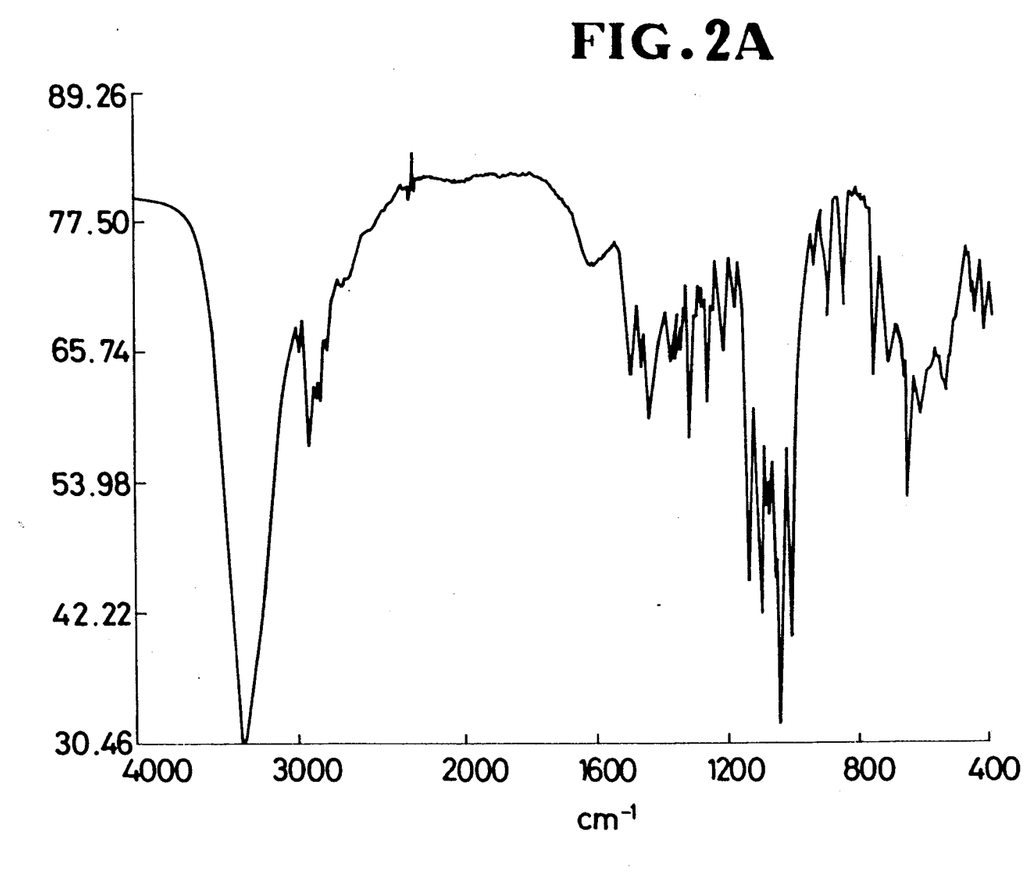
Figure 2B:
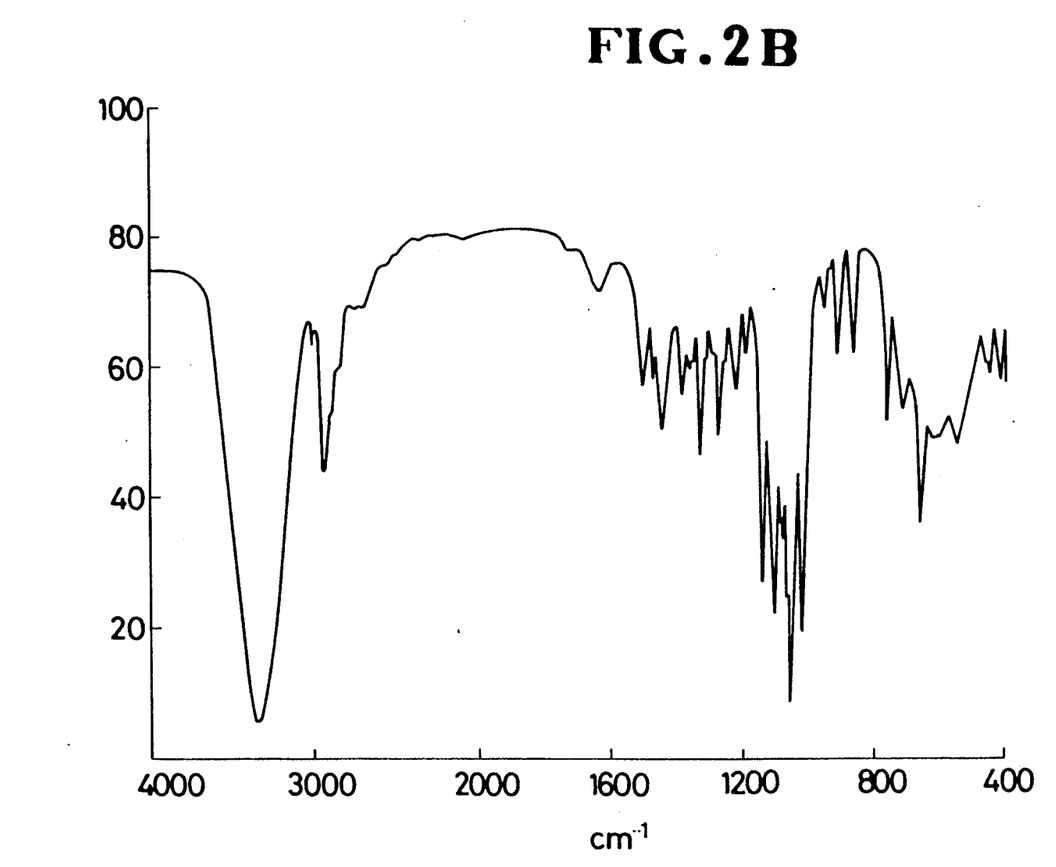
Figure 3A:
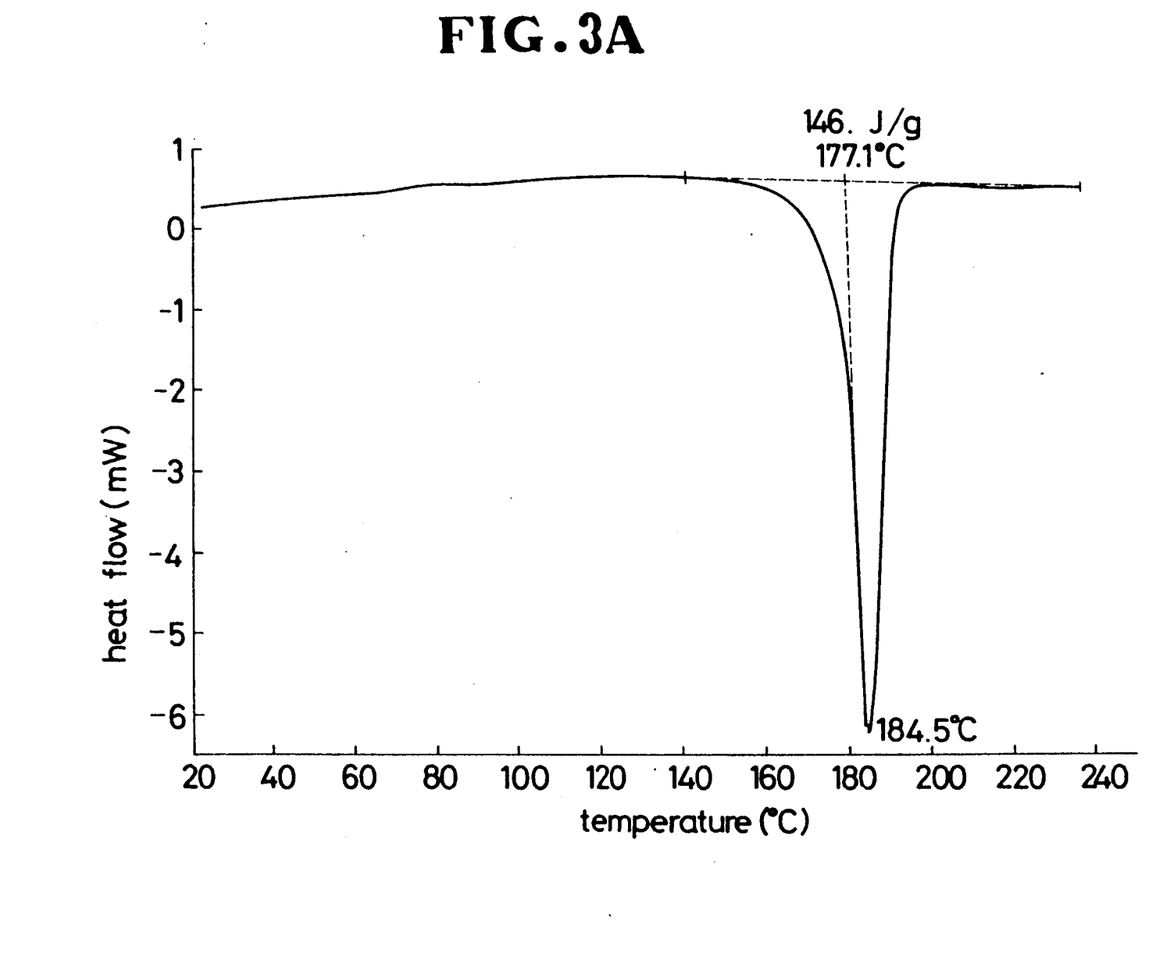
Figure 3B:
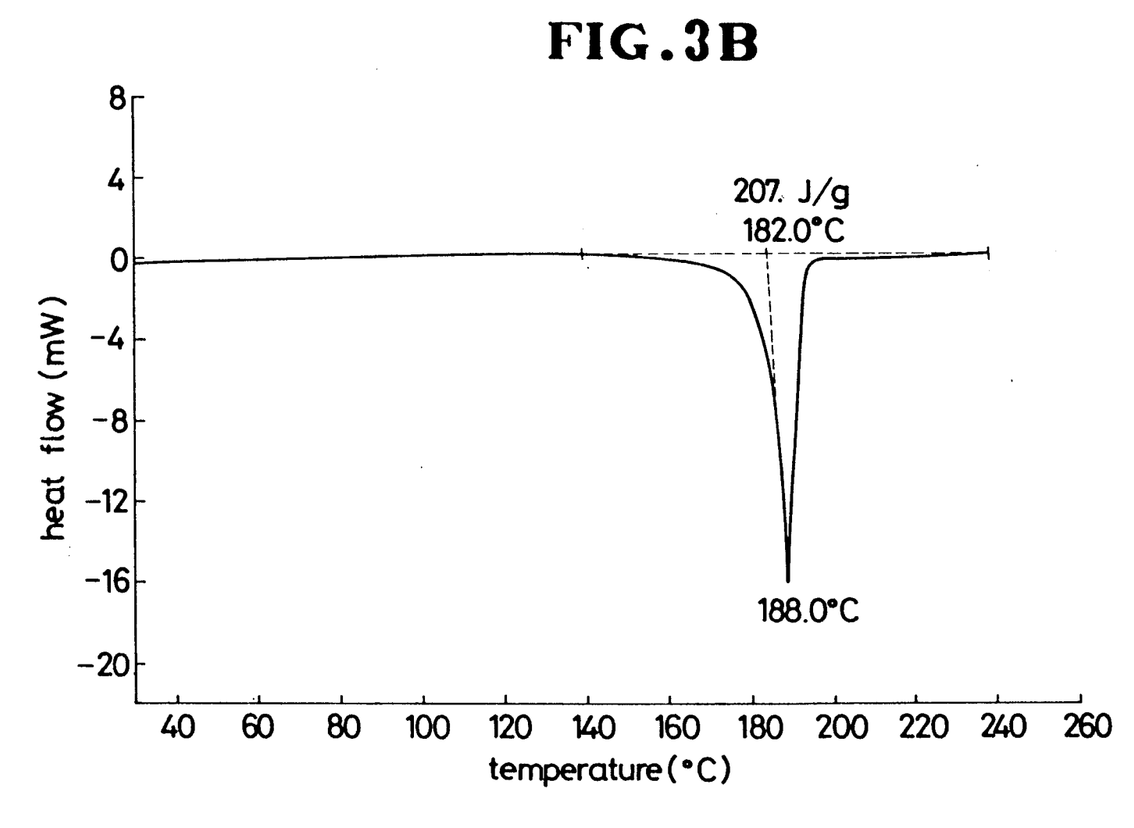
Figure 4A:
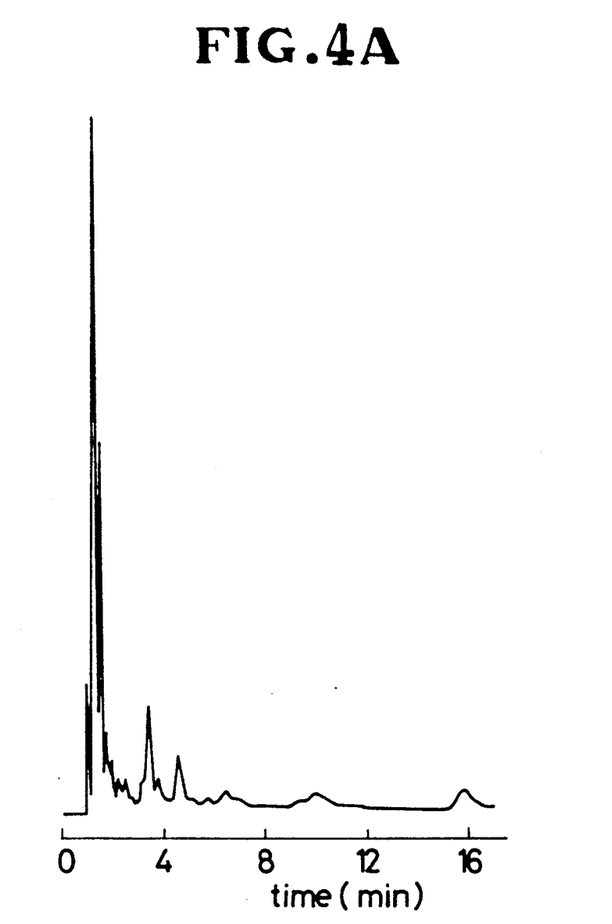
Figure 4B:
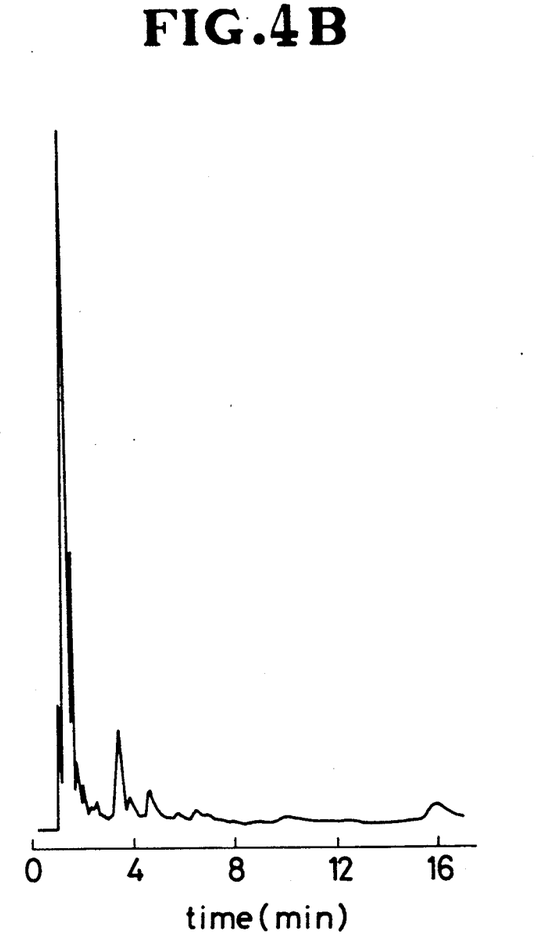
Figure 5A:
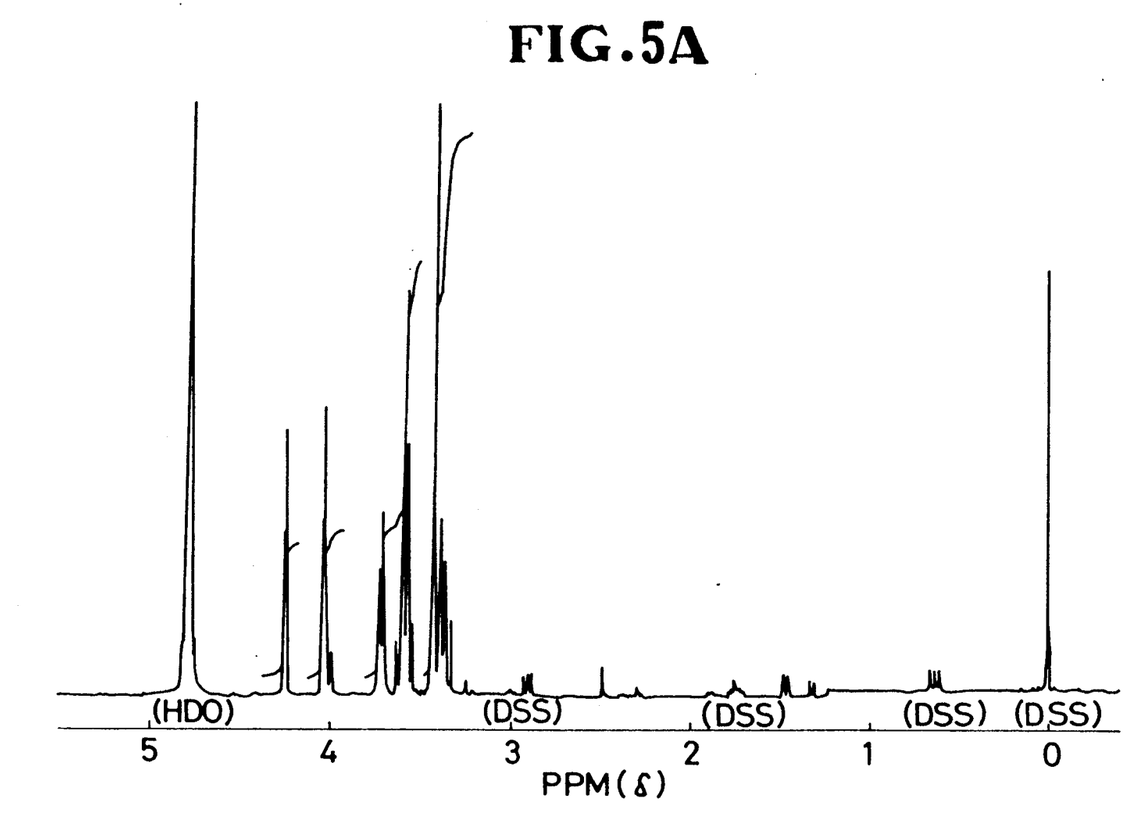
Figure 5B:
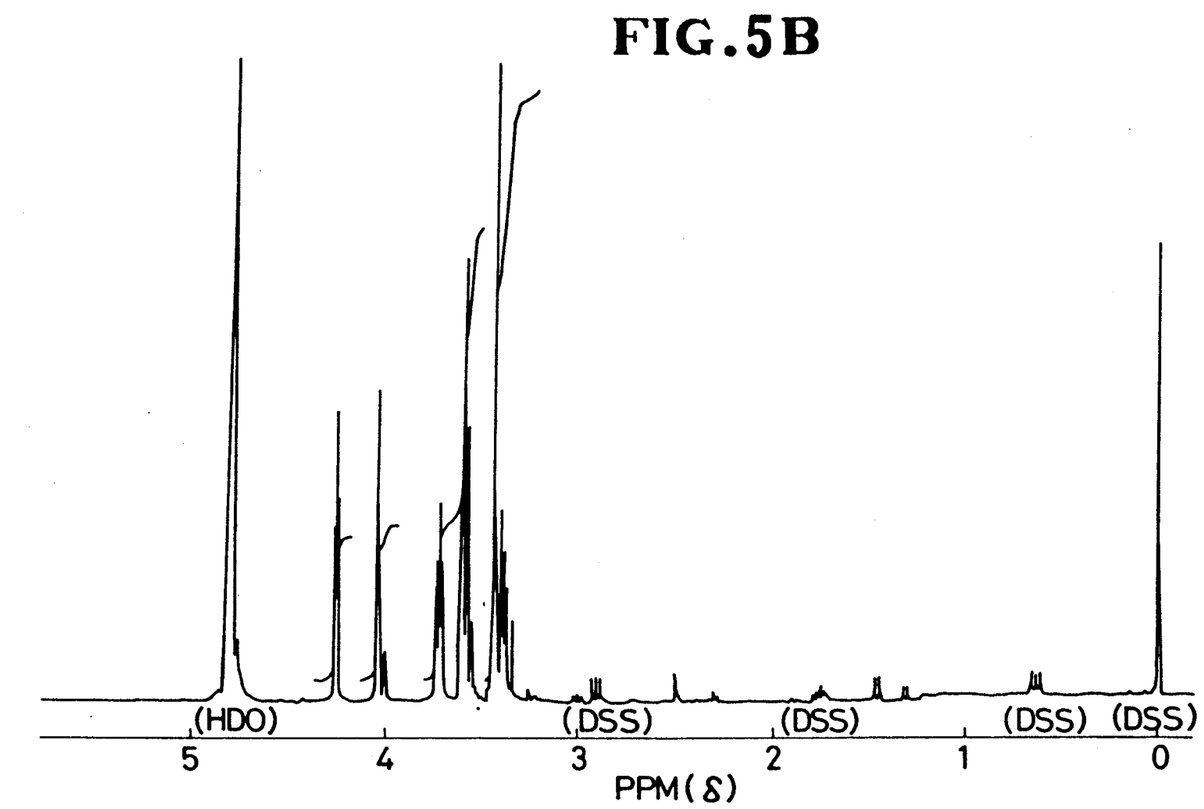
Figure 6:
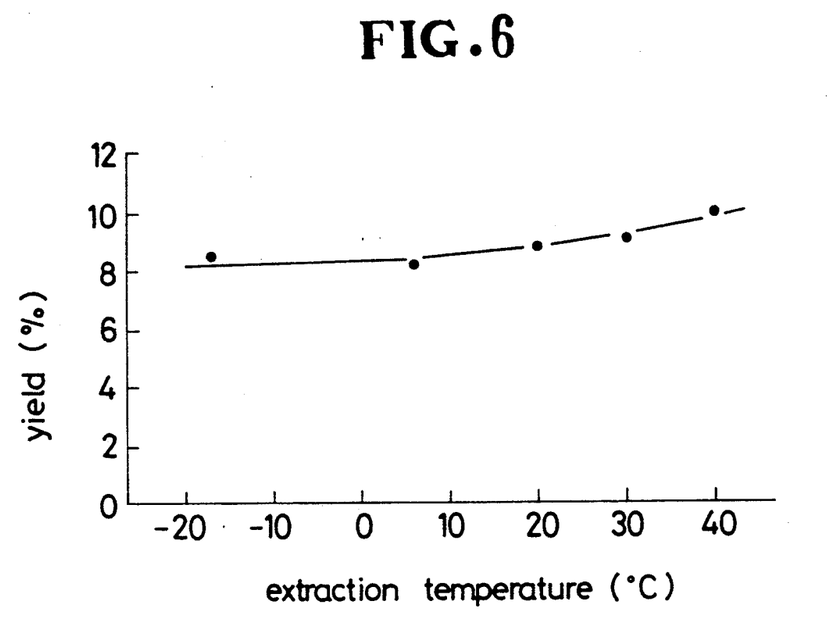
FIG. 6 and FIG. 7 are graphical representations of the yield and melting points of the compound, respectively, as plotted against the extraction temperature.
Figure 7:
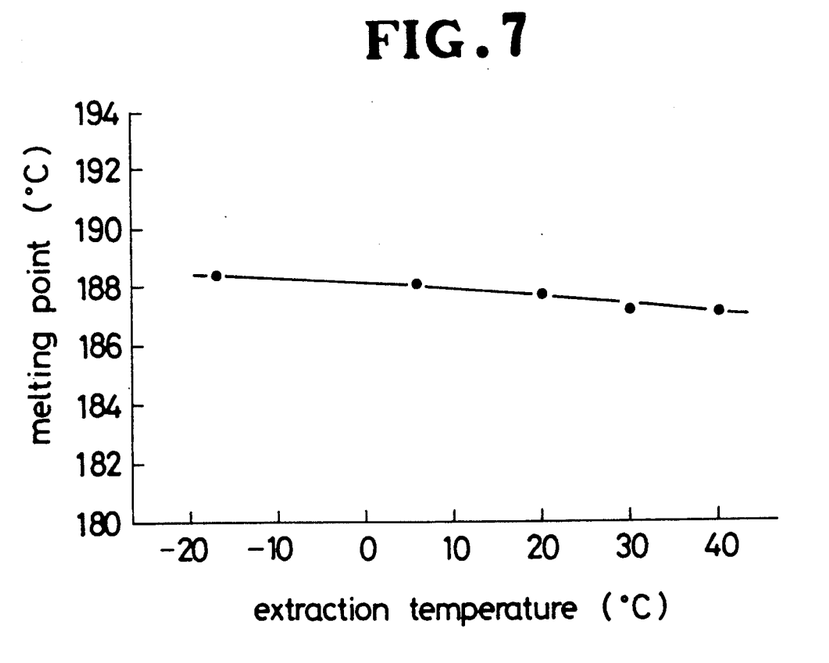

Higher temperatures have proved effective in increasing the yield but in an extent to gradually reduce the melt peak temperature. The specified range of extraction temperatures should be observed to attain improved efficiency.

While the invention has been described in conjunction with its specific embodiments, it should be noted that many changes and modifications may be made within the scope of the appended claims.

TABLE

| | methanol | | ethanol | |
| --- | --- | --- | --- | --- |
| | room temp. | boiling | room temp. | boiling |
| yield, g | 5.8 | 5.9 | 2.0 | 6.2 |
| (%) | (11.6) | (11.8) | (4.1) | (12.4) |
| color shade | white | slightly pale brown | slightly pale brown | pale brown |
| DSC melting behavior, °C. | | | | |
| initiation | 147.7 | 142.0 | 147.2 | 137.0 |
| peak | 189.4 | 188.6 | 189.7 | 188.0 |
| termination | 197.5 | 197.3 | 197.6 | 195.2 |
| appearance on extraction of serum dry solid | *1 | *2 | *3 | *4 |

*1 : Bulky mass easily broke fine.
*2 : Appearance was similar to that of *1.
*3 : Mass became highly viscous on its surface and hardly breakable even on exertion of force.
*4 : Mass broke with small lumps left.

What is claimed is:

1. A method for extracting L-quebrachitol from a rubber latex serum, which comprises concentrating the serum to form a concentrated serum product, dissolving the resulting serum product in methanol at a temperature of from −20° to 40° C. to form a solution and extract L-quebrachitol from the serum product, concentrating the solution to form a crystalline deposit of the L-quebrachitol extract and thereafter separating and collecting the extract from the solution.

2. The method of claim 1, including further purifying the extract with ethanol.

3. The method of claim 1, wherein the methanol is anhydrous or contains up to 30% water.

4. The method of claim 1, wherein the methanol is used in an amount of from 200 to 1,000 ml per 100 g of the serum product.

5. The method of claim 1, wherein the concentrated serum product is in the form of a dry pulverized solid.

6. The method of claim 1, wherein the concentrated serum product is in the form of a concentrated solution of the serum.

7. The method of claim 1, wherein the extraction is carried out as a temperature of from 10° to 22° C.

* * * * *